United States Patent
Zhao et al.

(10) Patent No.: US 11,583,656 B2
(45) Date of Patent: Feb. 21, 2023

(54) SYSTEM AND METHOD OF COUPLING ACOUSTIC AND ELECTRICAL STIMULATION OF NONINVASIVE NEUROMODULATION FOR DIAGNOSIS AND/OR TREATMENT

(71) Applicants: Yong D. Zhao, Simi Valley, CA (US); Jennifer Jinping Zhao, Simi Valley, CA (US)

(72) Inventors: Yong D. Zhao, Simi Valley, CA (US); Jennifer Jinping Zhao, Simi Valley, CA (US)

( * ) Notice: Subject to any disclaimer, the term of this patent is extended or adjusted under 35 U.S.C. 154(b) by 633 days.

(21) Appl. No.: 16/553,999

(22) Filed: Aug. 28, 2019

(65) Prior Publication Data

US 2021/0060289 A1 Mar. 4, 2021

(51) Int. Cl.
*A61M 21/00* (2006.01)
*A61M 21/02* (2006.01)
*A61N 1/36* (2006.01)

(52) U.S. Cl.
CPC ......... *A61M 21/02* (2013.01); *A61N 1/36014* (2013.01); *A61M 2021/0027* (2013.01); *A61M 2021/0072* (2013.01); *A61M 2205/50* (2013.01)

(58) Field of Classification Search
CPC .......................... A61N 1/36014; A61N 1/0534
USPC .......................................... 600/26–28; 607/66
See application file for complete search history.

(56) References Cited

U.S. PATENT DOCUMENTS

| | | | |
|---|---|---|---|
| 4,305,402 A | * | 12/1981 | Katims .............. A61N 1/36025 607/54 |
| 8,834,346 B2 | | 9/2014 | Henke et al. |
| 9,486,389 B2 | | 11/2016 | Tass |
| 10,098,539 B2 | | 10/2018 | Konofagou et al. |
| 2015/0297444 A1 | | 10/2015 | Tass |
| 2016/0001096 A1 | | 1/2016 | Mishelevich |
| 2016/0346545 A1 | * | 12/2016 | Pal ..................... A61N 1/36025 |
| 2017/0087364 A1 | * | 3/2017 | Cartledge ................ A61N 1/18 |
| 2019/0240468 A1 | * | 8/2019 | Yun ..................... A61N 1/36014 |

FOREIGN PATENT DOCUMENTS

| | | |
|---|---|---|
| WO | 2017149438 A1 | 9/2017 |
| WO | WO2017149438 A1 | 9/2017 |

* cited by examiner

*Primary Examiner* — Kaylee R Wilson

(57) ABSTRACT

A system and method of coupling acoustic and electrical stimulation of noninvasive neuromodulation is a therapeutic system and method preferably designed for the diagnosis and/or treatment of neurodegenerative diseases and neurological disorders including, but not limited to, tinnitus, hyperacusis, sleep disorder, depression, anxiety, dizziness, migraine, or ear suffocation. The system includes acoustic signal devices for deep brain electrical stimulation and electrical pulse devices for shallow brain electrical stimulation. Further, the system includes a signal-coupling module that includes an algorithm for coupling acoustic signals to electrical pulses. Parameters of each the acoustic signals and the electrical pulses are adjusted in order for the acoustic signals to be coupled to the electrical pulses. These parameters can also be adjusted based on patient feedback. Furthermore, the system can synchronously output the coupled acoustic signals and the coupled electrical pulses, asynchronously output the acoustic signals, or the electrical pulses based on patient feedback.

15 Claims, 15 Drawing Sheets

SYSTEM AND METHOD OF COUPLING ACOUSTIC AND ELECTRICAL STIMULATION OF NONINVASIVE NEUROMODULATION FOR DIAGNOSIS AND/OR TREATMENT

FIELD OF THE INVENTION

The present invention relates generally to electrophysiological therapy. More specifically, the present invention is a system and method that couples acoustic and electrical stimulation of noninvasive neuromodulation for diagnosis and/or treatment.

BACKGROUND OF THE INVENTION

Neurodegenerative diseases and neurological disorders such as, not limited to, tinnitus, hyperacusis, sleep disorder, depression, anxiety, dizziness, ear suffocation affect million of people worldwide. These neurodegenerative diseases and neurological disorders include symptoms which negatively affect neurons in the human brain, the spine, and head area of a human. There are various treatment methods for these types of diseases and disorders. Two of the most effective treatment methods include deep brain electrical stimulation and shallow brain electrical stimulation. Deep brain electrical stimulation is primarily provided through audio outputs, and shallow brain electrical stimulation is primarily provided through the electrical pulses. These two stimulation methods have been used separately and together for diagnosis and/or treatment of neurodegenerative diseases and neurological disorders. This has been proven effective, but there is still room for improvement.

Therefore, the objective of the present invention is to improve the diagnosis and/or treatment of neurodegenerative diseases and neurological disorders by coupling acoustic and electrical stimulation of noninvasive neuromodulation. The noninvasive neuromodulation approach is formed by means of the coupled and automatic adjustable deep brain electrical stimulation and shallow brain electrical stimulation systems. The deep brain electrical stimulation is by means of an external acoustic stimulation, whose acoustic signals are delivered to the ear canal via the headphone or speaker, and then are converted to the electrical signals by means of the cochlea, the electrical signals transmit through the auditory pathways and nonauditory pathways in the deep brain, the electrical signals modulate the neurological systems, improving the nerve noise signal filter function, activating neuron firing to form the nerve pulses transmitting through the nerves, desynchronizing abnormal signals generated by the neurological disorders, and thus reducing or eliminating the neurological disorder signals. The auditory pathways are of the thalamus, primary auditor cortex, secondary auditory cortex, anterior auditory field, peripheral system, etc. for the auditory functions. The nonauditory pathways are of the hippocampus amygdale for the memory and emotion functions, the somatosensory pathways for sensing, and the cingulate gyms for attention and consciousness.

DETAIL DESCRIPTIONS OF THE INVENTION

All illustrations of the drawings are for the purpose of describing selected versions of the present invention and are not intended to limit the scope of the present invention.

Figure 1:
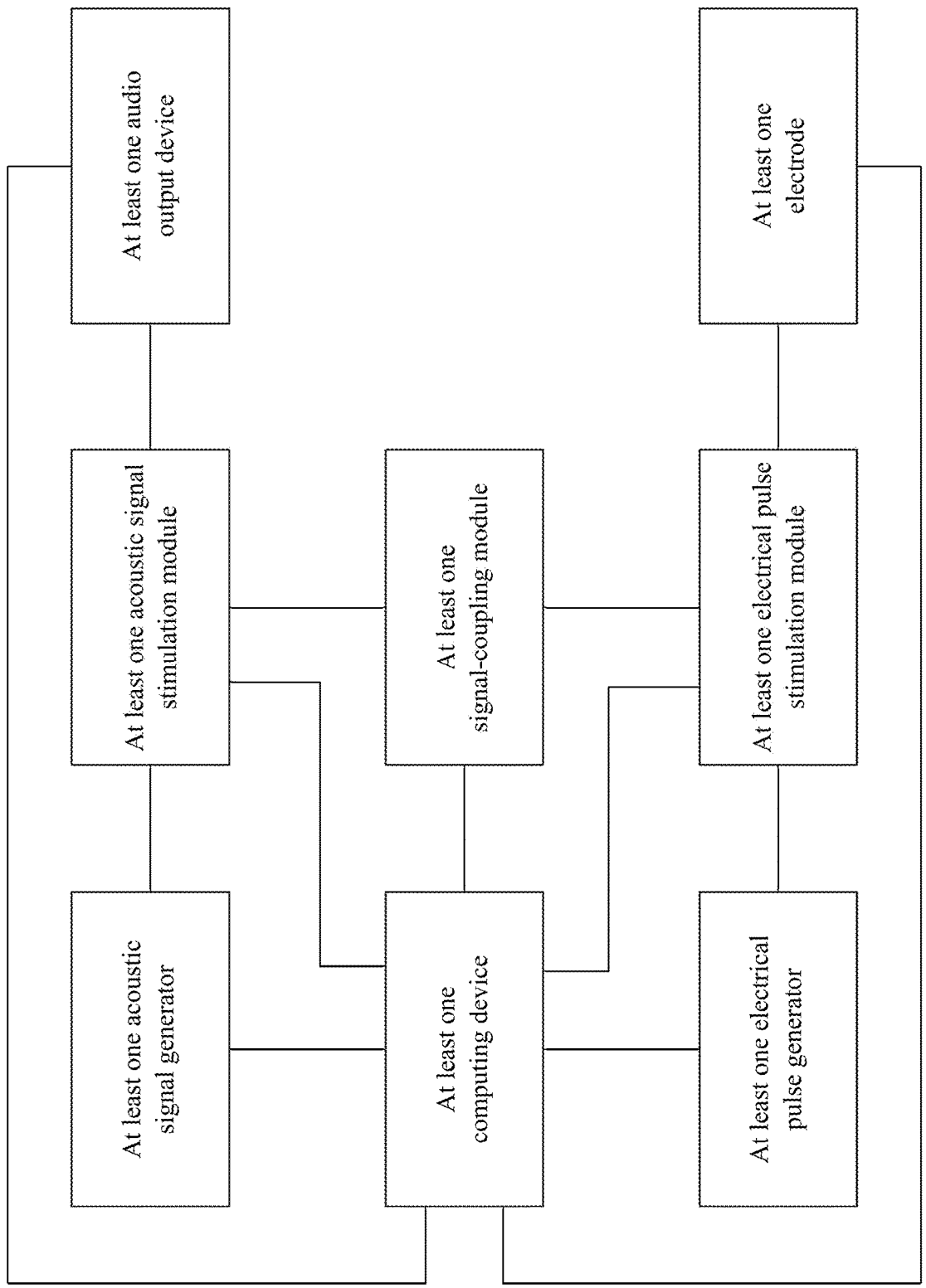
FIG. 1 is a schematic diagram illustrating the system of the present invention.

In reference to FIGS. 1 through 12, the present invention is a system and method of coupling acoustic and electrical stimulation of noninvasive neuromodulation for diagnosis and/or treatment. Further, the present invention is a therapeutic method preferably designed for the treatment of neurodegenerative diseases and neurological disorders including, but not limited to, tinnitus, hyperacusis, sleep disorder, depression, anxiety, dizziness, migraine, or ear suffocation. The present invention is conceptualized by the use of coupled and automatic adjustable deep brain electrical stimulation and shallow brain electrical stimulation systems. With reference to FIG. 1, the system of the present invention includes at least one acoustic signal generator, at least one acoustic signal stimulation module, at least one audio output device, at least one computing device, at least one electrical pulse generator, at least one electrical pulse stimulation module, at least one electrode and at least signal-coupling module.

Figure 2A:
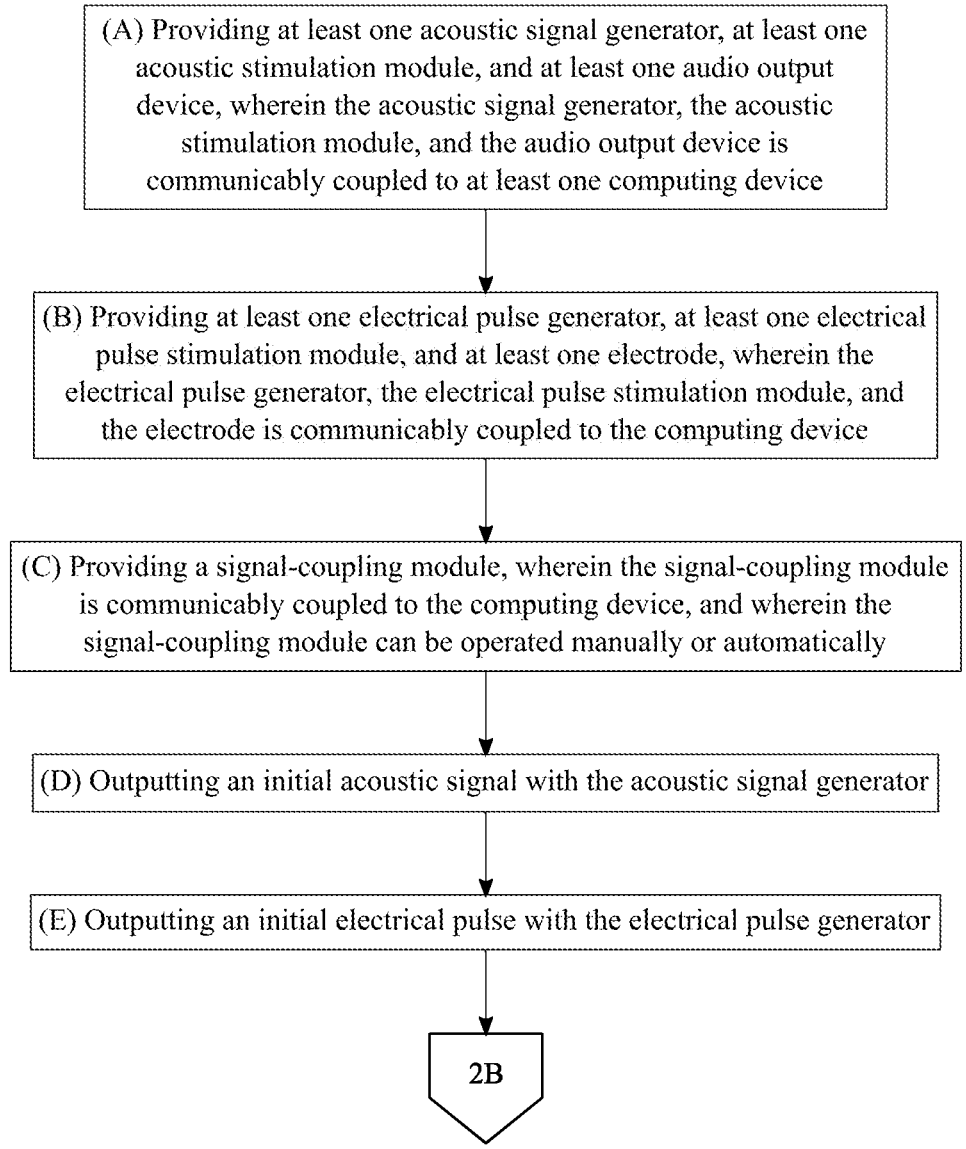
FIG. 2A is a flowchart illustrating the overall process of the present invention.

With reference to FIG. 2A, the acoustic signal generator, the acoustic signal stimulation module, and the audio output device are communicably coupled to at least one computing device (Step A). Thus, the computing device can be used to manually or automatically manage and control the acoustic signal generator, the acoustic signal stimulation module, and the audio output device. The computing device may be any device such as, but not limited to, a personal desktop computer, a mobile device, or an electronic tablet. Preferably, the computing device is a conventional module of device management and control. The acoustic signal generator may be any device able to produce an acoustic signal such as, but not limited to, pure tones, noises, music, natural sounds, or composite sounds. The acoustic signal stimulation module may be any device able to adjust the parameters of the acoustic signal produced by the acoustic signal generator. The audio output device may be any device able to output the acoustic signal produced and adjusted respectively by the acoustic signal generator and the acoustic signal stimulation module. The acoustic signal generator, the acoustic signal stimulation module, and the audio output device are the components used for the deep brain electrical stimulation. In further detail, the acoustic signal is delivered to the ear canal(s) of a patient and then the acoustic signal is converted to an electrical signal by means of the patient's cochlea. The converted electrical signal modulates the neurological system which improves the nerve noise signal filter function, activates neuron firing to form the nerve pulses transmitting through the nerves, and desynchronizes abnormal signals generated by the neurological disorders, and thus reducing or eliminating the neurological disorder signals.

With reference to FIG. 2A, the electrical pulse generator, the electrical pulse stimulation module, and the electrode are communicably coupled to the computing device (Step B). Thus, the computing device can be used to manually or automatically manage and control the electrical pulse generator, the electrical pulse stimulation module, and the electrode. The electrical pulse generator may be any device able to produce electrical pulses for electrical stimulation such as, but not limited to, transcranial direct current stimulation (tDCS). The electrical pulse stimulation module may be any device able to adjust the parameters of the electrical pulse produced by the electrical pulse generator. The electrode may be any device able to output the electrical pulse produced and adjusted respectively by the electrical pulse generator and the electrical pulse stimulation module. The electrical pulse generator, the electrical pulse stimulation module, and the electrode are the components used for the shallow brain stimulation. In further detail, electrical pulses produced by the electrical pulse generator are transmitted through the electrode(s) which can be placed at up to 200 multiple spots on the head, neck, and body skin surface. The number of electrodes, the target spots to place the electrodes, the direct current pulse parameters of wave shape, amplitude, width, delay, etc. can be defined independently by in vitro or in vivo experiments, as well as by massage stimulation or electrical circuitry modeling.

With reference to FIG. 2A, the signal-coupling module is communicably coupled to the computing device (Step C). This allows the signal-coupling module to be operated manually or automatically. Thus, the user can manually control and mange the signal-coupling module or input settings to have the signal-coupling module to function automatically. The signal-coupling module is used to compare acoustic signals to electrical pulses in order to synchronize the acoustic signals to the electrical pulses.

Figure 2B:
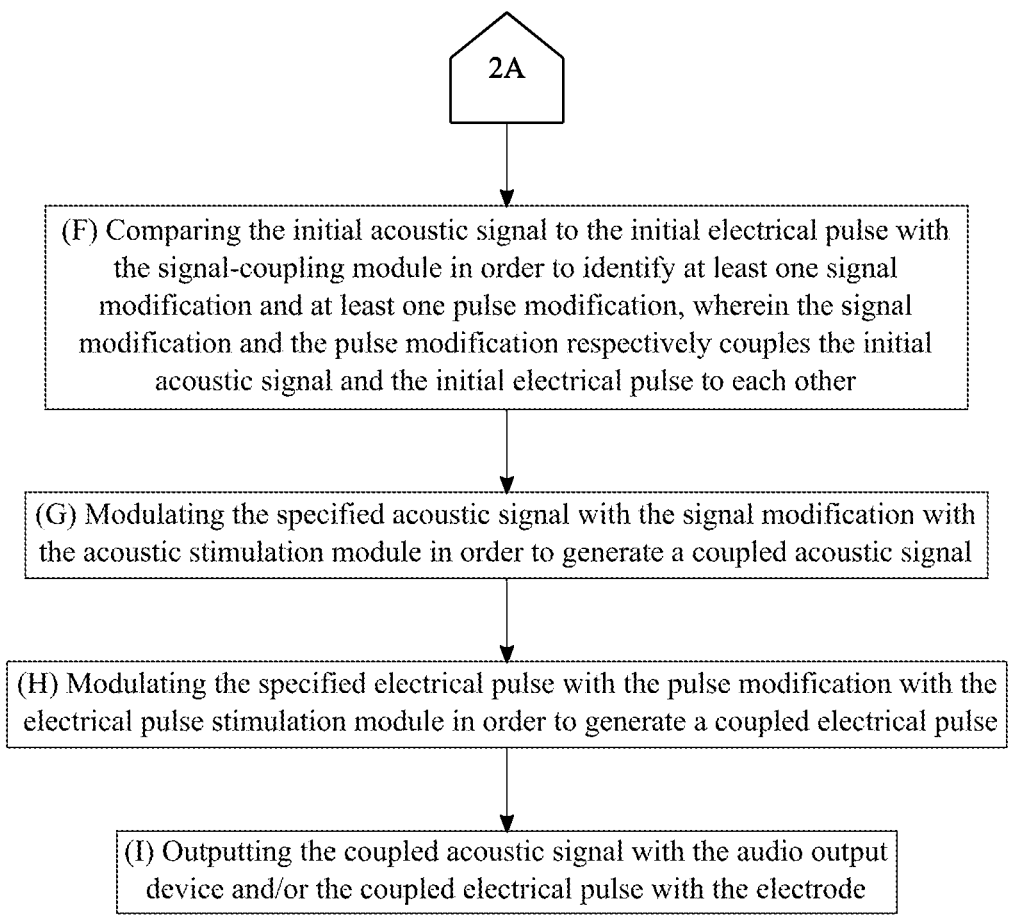
FIG. 2B is a continuation of the flowchart from FIG. 2A.

With reference to FIGS. 2A and 2B, the method of the present invention follows an overall process that allows coupling of acoustic and electrical stimulation of noninvasive neuromodulation for diagnosis and/or treatment. The acoustic signal generator is used to output an initial acoustic signal (Step D). The initial acoustic signal is a non-adjusted acoustic signal produced by the acoustic signal generator. The electrical pulse generator is used to output an initial electrical pulse (Step E). The initial electrical pulse is a non-adjusted electrical pulse produced by the electrical pulse generator. The signal-coupling module is used to compare the initial acoustic signal to the initial electrical pulse in order to identify at least one signal modification and at least one pulse modification (Step F). The signal modification and the pulse modification are used to respectively couple the initial acoustic signal and the initial electrical pulse to each other. The signal modification is a change to a parameter of the initial acoustic signal. The pulse modification is a change to a parameter of the initial electrical pulse. In further detail, Step F is performed to calculate what parameter changes of the initial acoustic signal and the initial electrical pulse are required to couple the initial acoustic signal to the initial electrical pulse. Moreover, the acoustic stimulation module is used to modulate the initial acoustic signal with the signal modification in order to generate a coupled acoustic signal (Step G). The initial acoustic signal is an acoustic signal produced by the acoustic signal generator chosen by a user. The coupled acoustic signal is an acoustic signal which has been adjusted to be coupled with an electrical pulse. The electrical pulse stimulation module is used to modulate the initial electrical pulse with the pulse modification in order to generate a coupled electrical pulse (Step H). The initial electrical pulse is an electrical pulse produced by the electrical pulse generator chosen by a user. The coupled electrical pulse is an electrical pulse which has been adjusted to be coupled with an acoustic signal. The audio output device is used to output the coupled acoustic signal and/or the electrode is used to output the coupled electrical pulse (Step I). This step facilitates the deep brain electrical stimulation and/or the shallow brain electrical stimulation onto a patient.

Figure 3:
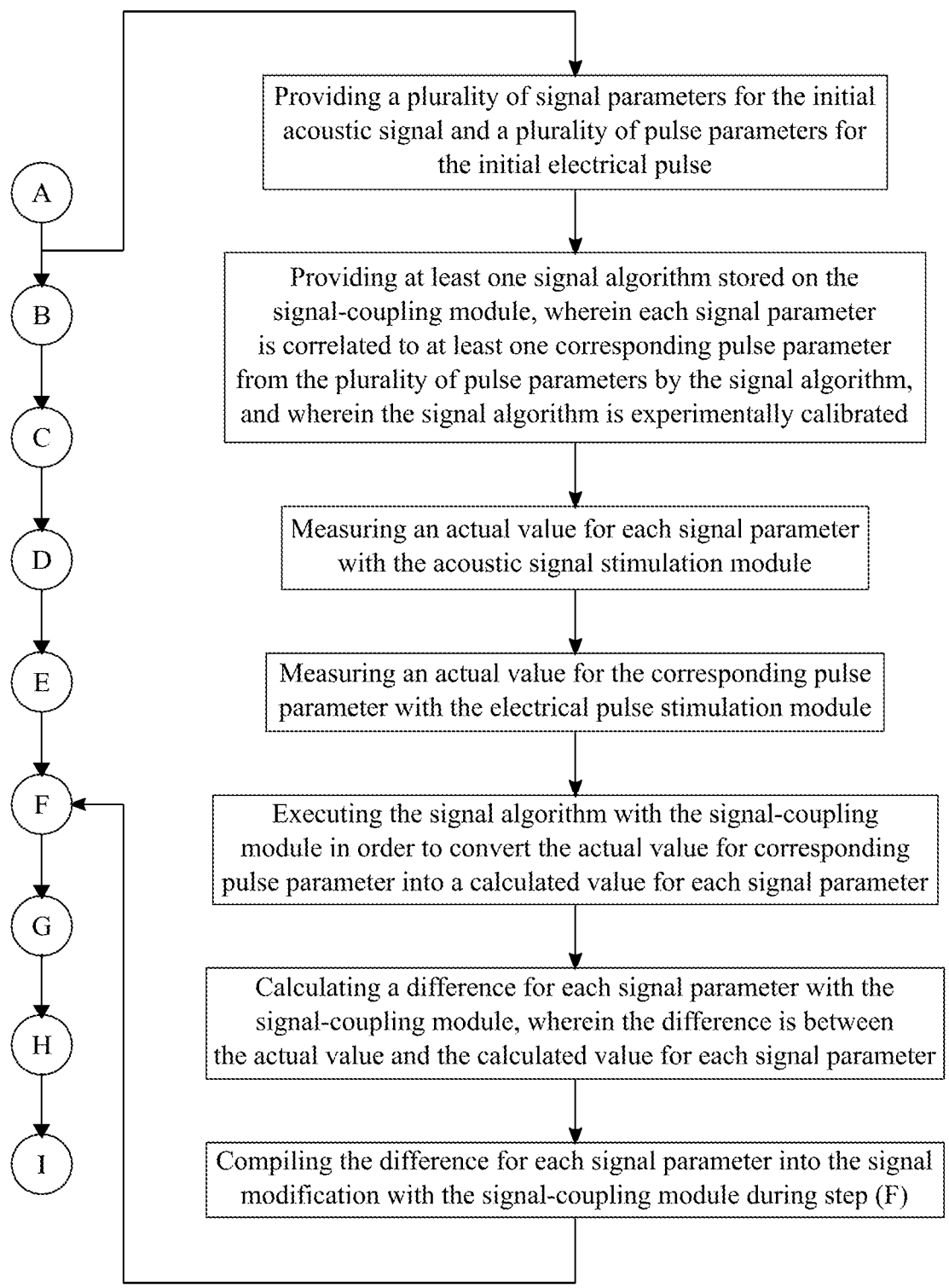
FIG. 3 is a flowchart illustrating the subprocess for calculating the signal modification.

With reference to FIG. 3, the following subprocess is used to calculate the signal modification. A plurality of signal parameters is provided for the initial acoustic signal, and a plurality of pulse parameters is provided for the initial electrical pulse. The plurality of signal parameters includes, but is not limited to, loudness, frequency, pitch, melody, and modulation. The plurality of pulse parameters includes, but is not limited to, wave shape, amplitude, width, and delay. At least one signal algorithm is provided for this subprocess and is stored on the signal-coupling module. Each signal parameter is correlated to at least one corresponding pulse parameter from the plurality of pulse parameters by the signal algorithm. The signal algorithm is experimentally calibrated in order to properly correlate a signal parameter to a pulse parameter. The acoustic stimulation module is used to measure an actual value for each signal parameter. The actual value for each signal parameter a live reading represented in measurement units of a signal parameter for the initial acoustic signal. The electrical pulse stimulation module is used to measure an actual value for the corresponding pulse parameter. The actual value for the corresponding pulse parameter is a live reading represented in measurement units of a pulse parameter for the initial electrical pulse. The signal-coupling module is used to execute the signal algorithm in order to convert the actual value for the corresponding pulse parameter a calculated value for each signal parameter. The calculated value is the required value of each signal parameter in order for the acoustic signal to be coupled to the electrical pulse. The signal-coupling module is used to calculate a difference for each signal parameter. The difference is between the actual value and the calculated value for each signal parameter. In further detail, the difference is the adjustment required in a signal parameter in order to couple the acoustic signal to the electrical pulse. The signal-coupling module is used to compile the difference for each signal parameter into the signal modification during Step F. Thus, the signal parameters of the acoustic signal are coupled to the pulse parameters of the electrical pulse.

Figure 4:
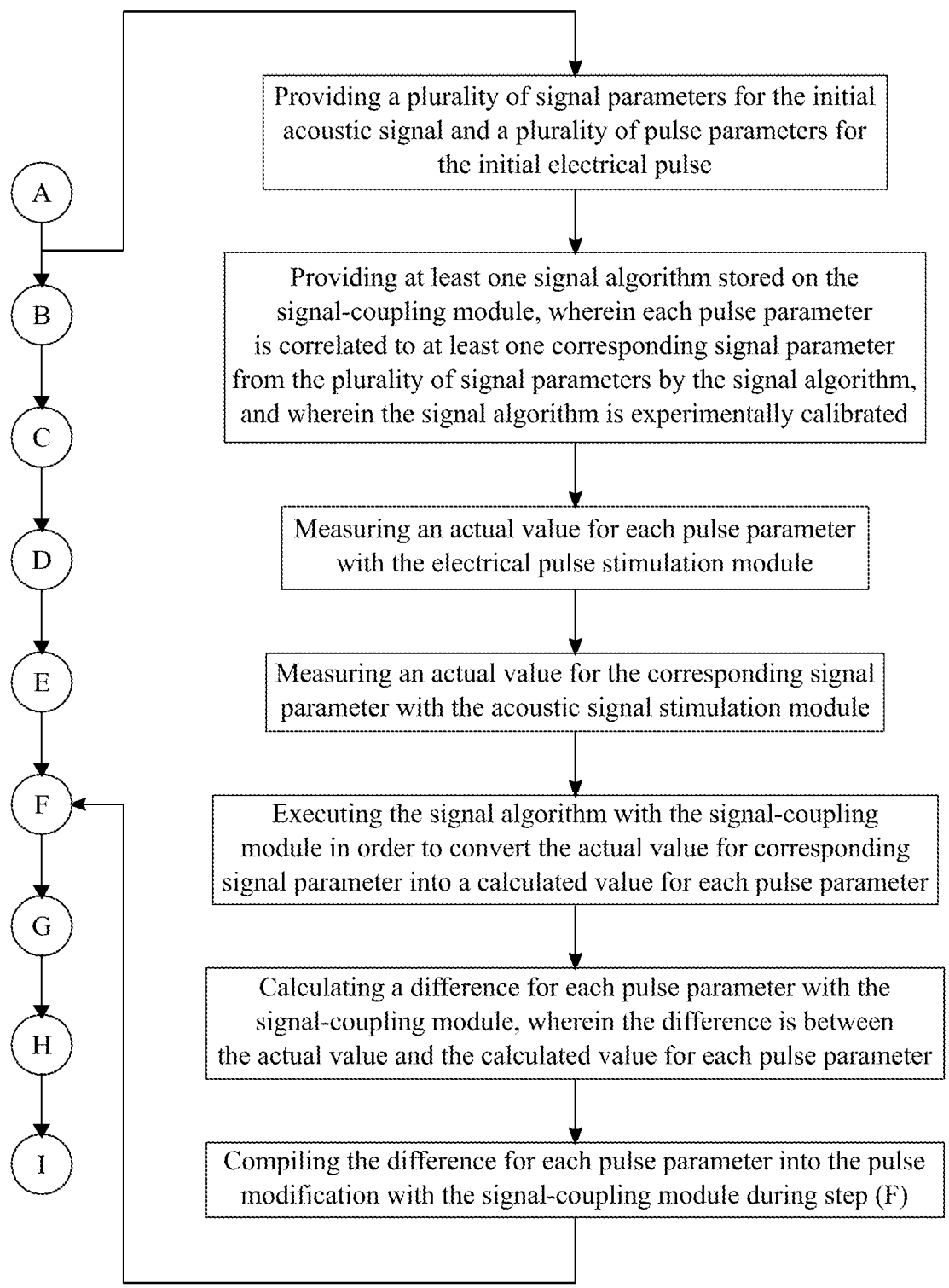
FIG. 4 is a flowchart illustrating the subprocess for calculating the pulse modification.

With reference to FIG. 4, the following subprocess is used to calculate the pulse modification. Similar to the subprocess for calculating the signal modification, at least one signal algorithm is provided for this subprocess and is stored on the signal-coupling module. Each pulse parameter is correlated to at least one corresponding signal parameter from the plurality of signal parameters by the signal algorithm. The signal algorithm is experimentally calibrated in order to properly correlate a pulse parameter to a signal parameter. The acoustic stimulation module is used to measure an actual value for each pulse parameter. The actual value for each pulse parameter is a live reading represented in measurement units of a pulse parameter for the initial electrical pulse. The acoustic signal stimulation module is used to measure an actual value for the corresponding signal parameter. The actual value for the corresponding signal parameter is a live reading represented in measurement units of a signal parameter for the initial acoustic signal. The signal-coupling module is used to execute the signal algorithm in order to convert the actual value for the corresponding signal parameter into a calculated value for each pulse parameter. The calculated value is the required value of each pulse parameter in order for the electrical pulse to be coupled to the acoustic signal. The signal-coupling module is used to calculate a difference for each pulse parameter. The difference is between the actual value and the calculated value for each pulse parameter. In further detail, the difference is the adjustment required in a pulse parameter in order to couple the electrical pulse to the acoustic signal. The signal-coupling module is used to compile the difference for each pulse parameter into the pulse modification during Step F. Thus, the pulse parameters of the electrical pulse are coupled to the signal parameters of the acoustic signal.

As mentioned previously, the audio output device may be any device about to output an acoustic signal. In one embodiment of the present invention, the audio output device is preferably a pair of headphones. The pair of headphones may be worn by a patient in order to receive the deep brain electrical stimulation. In another embodiment of the present invention, the audio output device is preferably at least one speaker. The speaker is used for a patient to receive the deep brain electrical stimulation.

In one embodiment of the present invention, the electrode is preferably a skin electrode. The skin electrode is physically connected to the skin of the patient to provide the shallow brain electrical stimulation. In another embodiment of the present invention, the electrode is preferably a transmucosal electrode. The transmucosal electrode is connected to mucous membrane of the patient to provide the shallow brain electrical stimulation.

Figure 5:
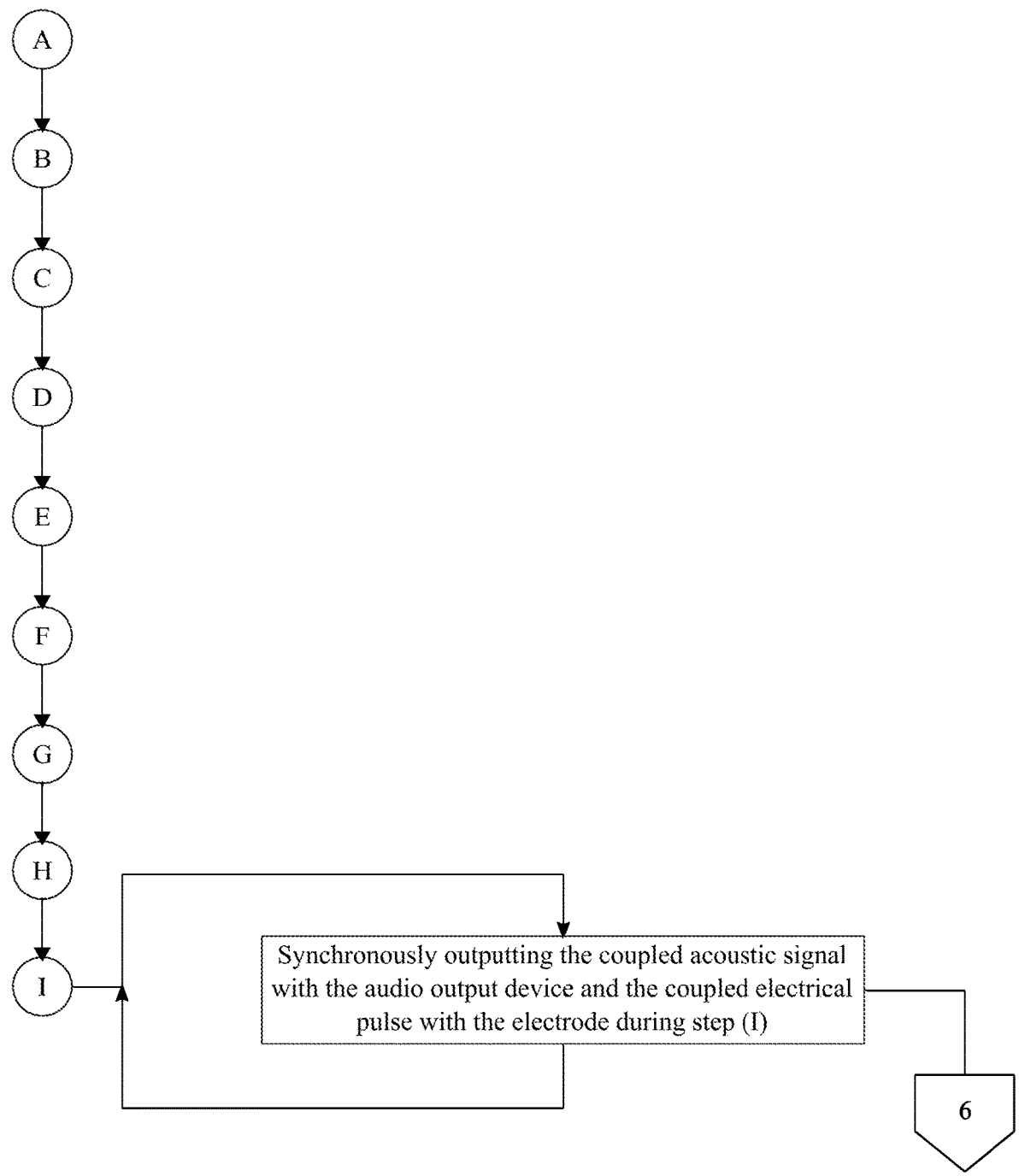
FIG. 5 is a flowchart illustrating the subprocess for the synchronous output of the coupled acoustic signal and the coupled electrical pulse.
Figure 6:
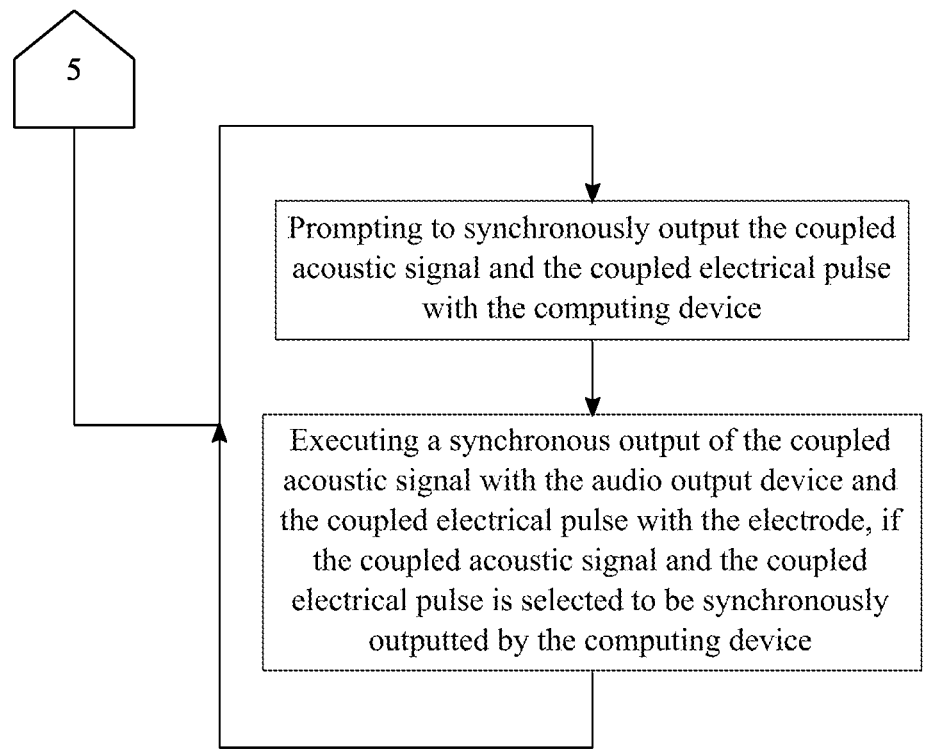
FIG. 6 is a flowchart illustrating the subprocess on how the synchronous output of the coupled acoustic signal and the coupled electrical pulse can be selected.

The present invention may be manually or automatically configured for different outputs. With reference to FIG. 5, the following subprocess allows the present invention to synchronously output the coupled acoustic signal and the coupled electrical pulse. The coupled acoustic signal and the coupled electrical pulse may be synchronously and respectively outputted with the audio output device and the electrode during Step I. In order for the present invention to synchronously output the coupled acoustic signal and the coupled electrical pulse and with reference to FIG. 6, the computing device prompts to synchronously output the coupled acoustic signal and the coupled electrical pulse. The synchronous output of the coupled acoustic signal with the audio output device and the coupled electrical pulse with the electrode is executed if the coupled acoustic signal and the coupled electrical pulse are selected to be synchronously outputted by the computing device. The synchronous output of the coupled acoustic signal and the electrical pulse is used to simultaneously provide the deep brain electrical stimulation and the shallow brain electrical stimulation to a patient.

Figure 7:
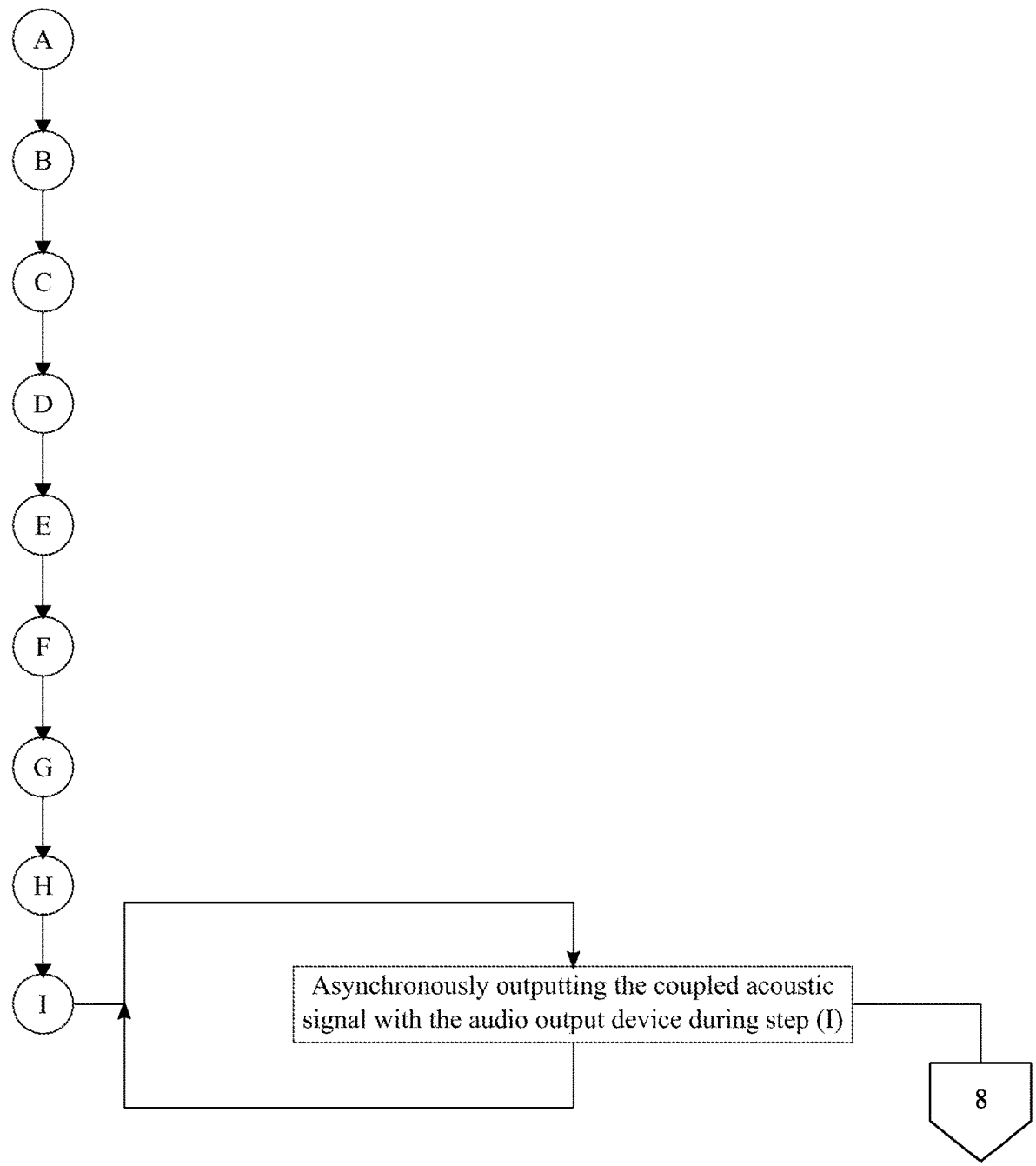
FIG. 7 is a flowchart illustrating the subprocess for the asynchronous output of the coupled acoustic signal.
Figure 8:
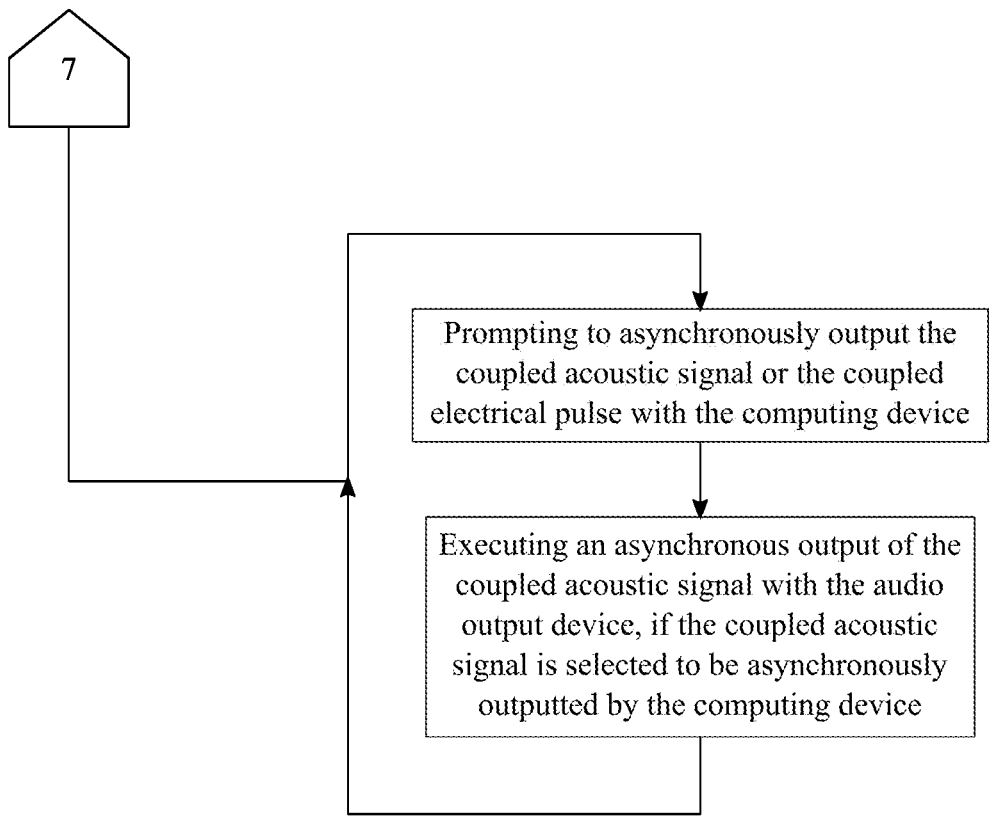
FIG. 8 is a flowchart illustrating the subprocess on how the asynchronous output of the coupled acoustic signal can be selected.

With reference to FIG. 7, the following subprocess allows the present invention to asynchronously output the coupled acoustic signal. The coupled acoustic signal may be asynchronously outputted with the audio output device during Step I. In order for the present invention to asynchronously output the coupled acoustic signal and with reference to FIG. 8, the computing device prompts to asynchronously output the coupled acoustic signal or the coupled electrical pulse. This step allows the user to actively choose whether or not to asynchronously output the coupled acoustic signal. The asynchronous output of the coupled acoustic signal with the audio output device is executed if the coupled acoustic signal is selected to be asynchronously outputted by the computing device. The asynchronous output of the coupled acoustic signal is used to solely provide the deep brain electrical stimulation.

Figure 9:
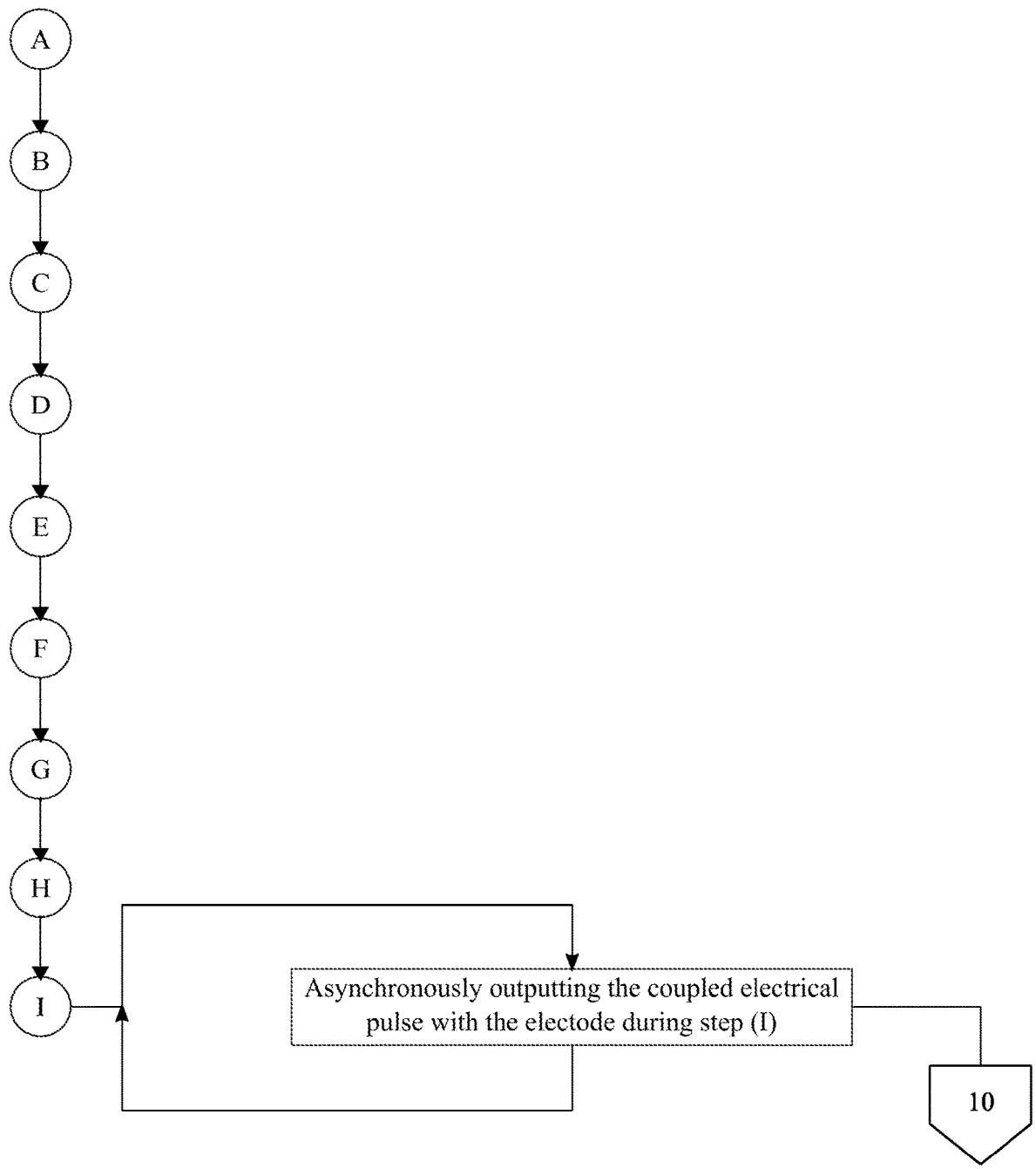
FIG. 9 is a flowchart illustrating the subprocess for the asynchronous output of the coupled electrical pulse.
Figure 10:
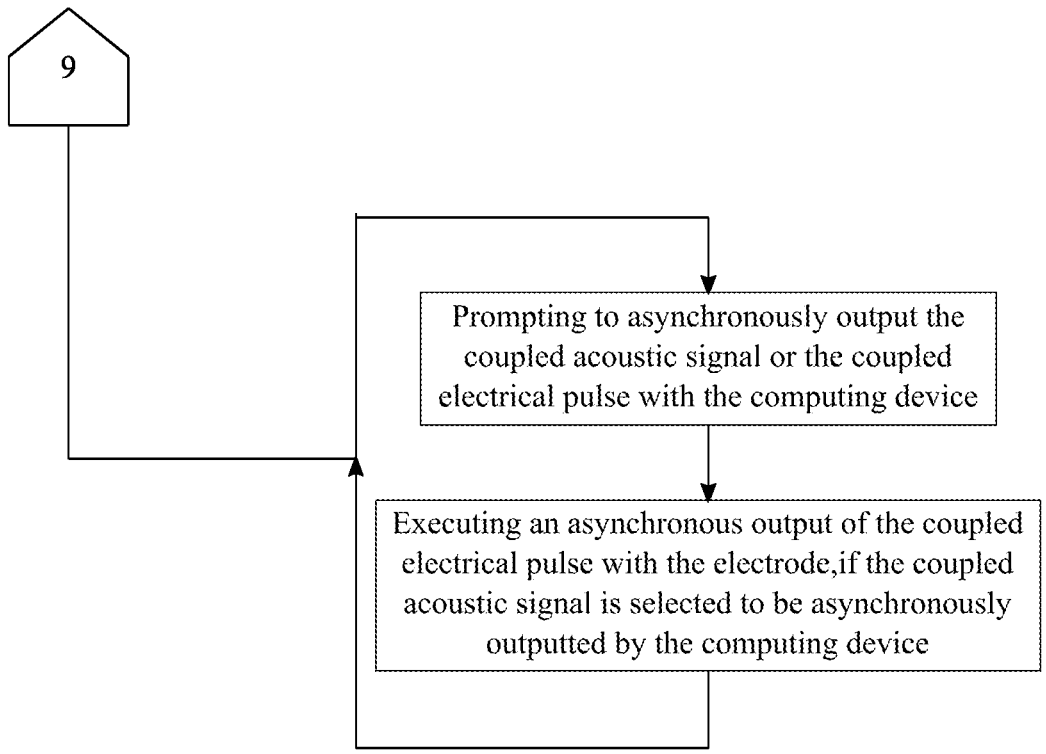
FIG. 10 is a flowchart illustrating the subprocess on how the asynchronous output of the coupled electrical pulse can be selected.

Alternatively and with reference to FIG. 9, the following subprocess allows the present invention to asynchronously output the coupled electrical pulse. The coupled electrical may be asynchronously outputted with the electrode device during Step I. In order for the present invention to asynchronously output the coupled electrical pulse and with reference to FIG. 10, the computing device prompts to asynchronously output the coupled acoustic signal or the coupled electrical pulse. This step allows the user to actively choose whether or not to asynchronously output the coupled electrical pulse. The asynchronous output of the coupled electrical pulse with the electrode is executed if the coupled electrical pulse is selected to be asynchronously outputted by the computing device. The asynchronous output of the coupled electrical pulse is used to solely provide the shallow brain electrical stimulation.

Figure 11A:
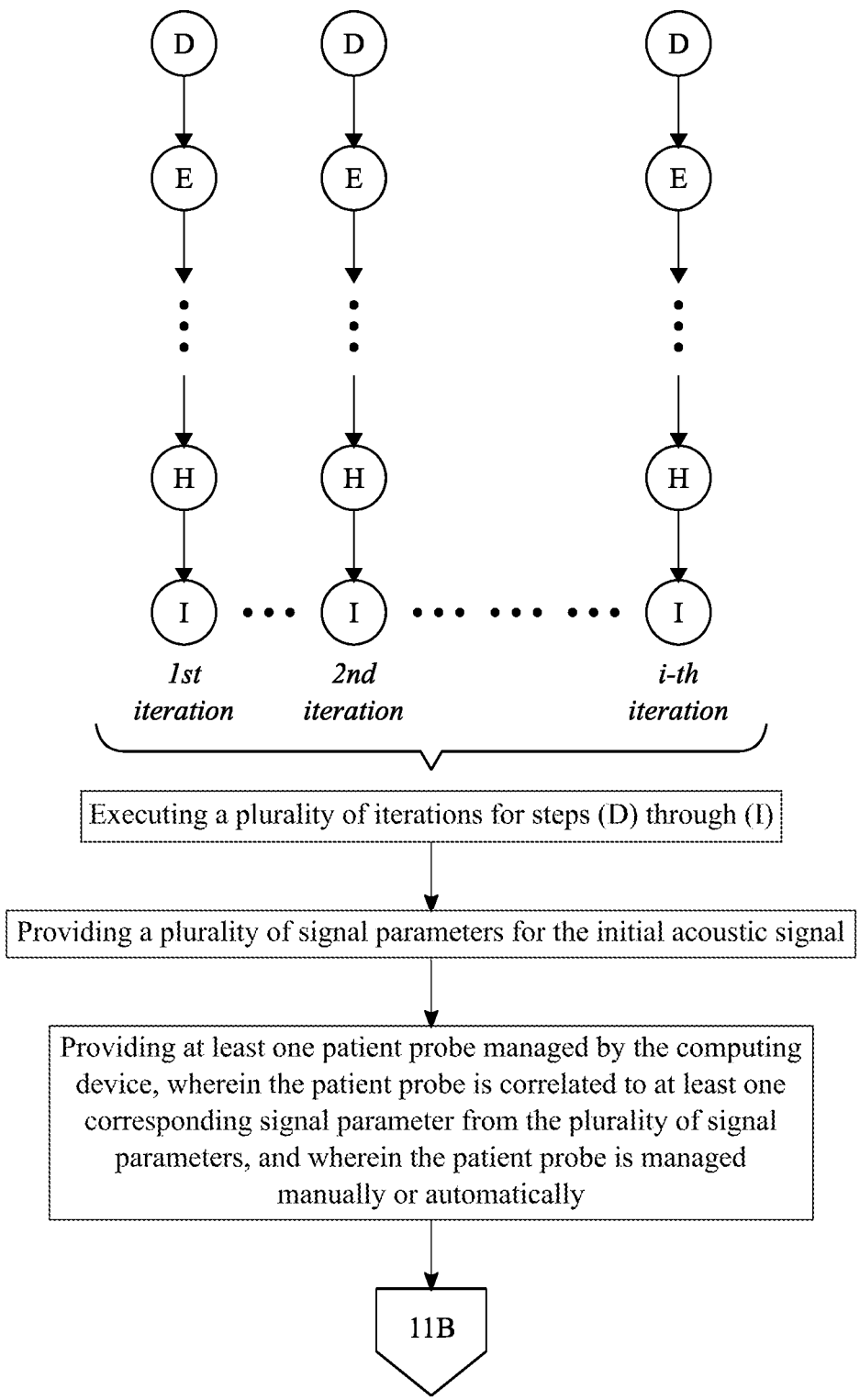
FIG. 11A is a flowchart illustrating the subprocess for determining the adjustments required for the acoustic signal to comfortably and positively affect the patient.
Figure 11B:
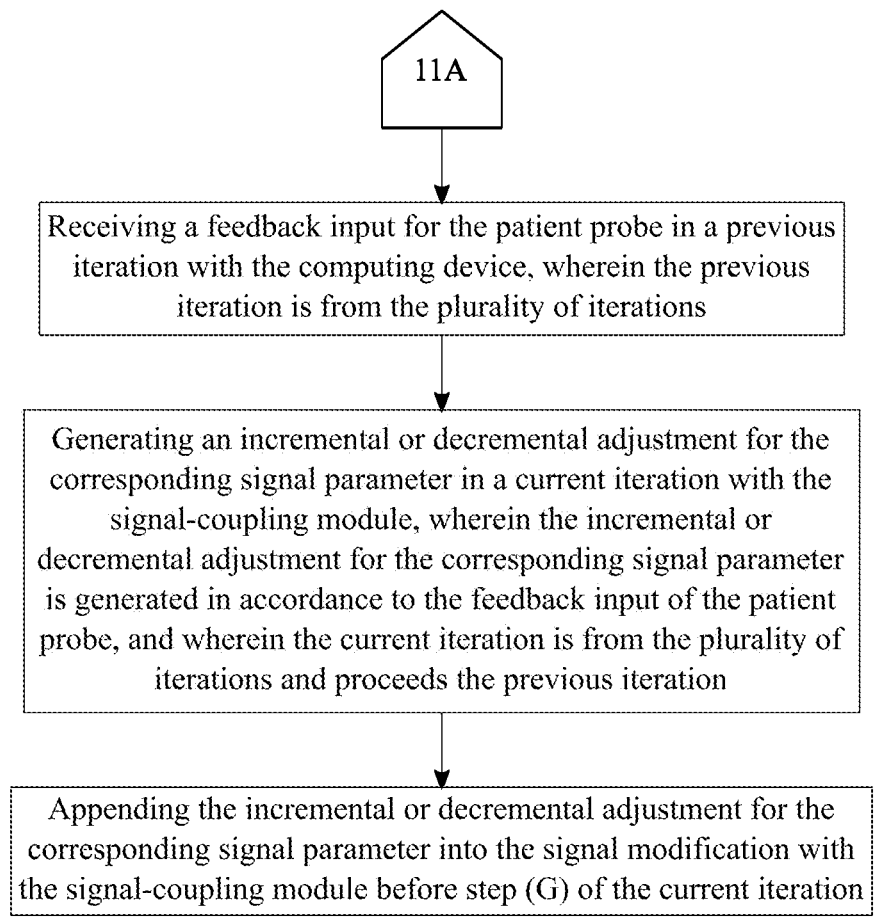
FIG. 11B is a continuation of FIG. 11A.

With reference to FIGS. 11A and 11B, the following subprocess determines the adjustments required for the acoustic signal to comfortably and positively affect the patient. A plurality of iterations is executed for Steps D through I. At least one patient probe is provided and managed by the computing device. The patient probe is correlated to at least one corresponding signal parameter from the plurality of signal parameters. The patient probe is managed manually or automatically. The patient probe may be information such as, but not limited to, patient subjective or objective feedback of the treatment effectiveness, comfortability treatment time duration, and other therapeutic requirements or evaluations. The computing device is used to receive a feedback input for the patient probe in a previous iteration. The feedback input may be any information retrieved following the patient probe such as, but not limited to, a verbal response from the patient or a visual observation of the patient. The previous iteration is from the plurality of iterations. The signal-coupling module is used to generate an incremental or decremental adjustment for the corresponding signal parameter in a current iteration. The incremental or decremental adjustment for the corresponding signal parameter is generated in accordance to the feedback of the patient probe. The current iteration is from the plurality of iterations and proceeds the previous iteration. In further detail and in the preferred embodiment, the acoustic signal modulation of the signal parameters such as, but not limited to, amplitude, frequency, and combination of both the amplitude and frequency is based on the input modulating waveforms including, but not limited to, trigonometric, sinusoidal, square waveforms. The amplitude typically within 30% of the tested hearing threshold is adjusted in step of less than 5 dBs for the amplitude modulation (AM) procession. The frequency change range is typically less than 50 Hz and is adjusted in step of less than 5 Hz for the frequency modulation (FM) procession. The target acoustic signals, which are the hearing threshold or the carrier signals combined with the modulated signals, wave shapes, background sounds or music, are combined and emitted in one or up to 10 frequency bands that are within a bandwidth up to 1000 Hz and adjusted in step of 1 Hz-100 Hz around the band center frequencies or tinnitus frequency points obtained with the tinnitus sound matching tests or psychoacoustic testing of tinnitus. The total acoustic loudness is less than 120 dBs, and acoustic frequency range is 0-20 kHz for the acoustic stimulation therapies. The signal-coupling module is used to append the incremental or decremental adjustment for the corresponding signal parameter into the signal modification before Step G of the current iteration. Thus, the acoustic signal is adjusted to be comfortable and positively-effective for the patient. As disclosed previously, the incremental or decremental adjustment is minimally and maximally limited within the specified parameter range of the corresponding signal parameter.

Figure 12A:
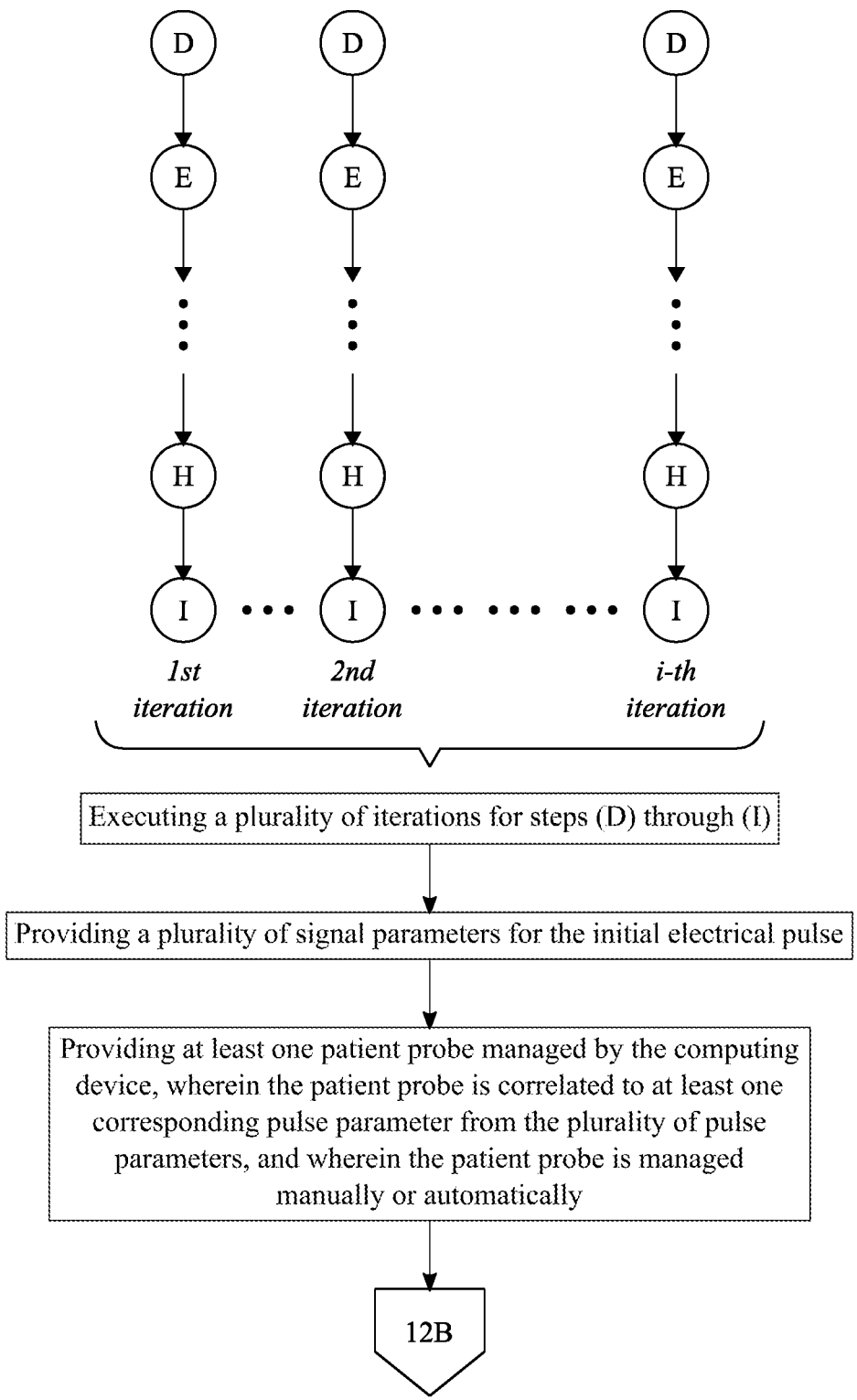
FIG. 12A is a flowchart illustrating the subprocess for determining the adjustments required for the electrical pulse to comfortably and positively affect the patient.
Figure 12B:
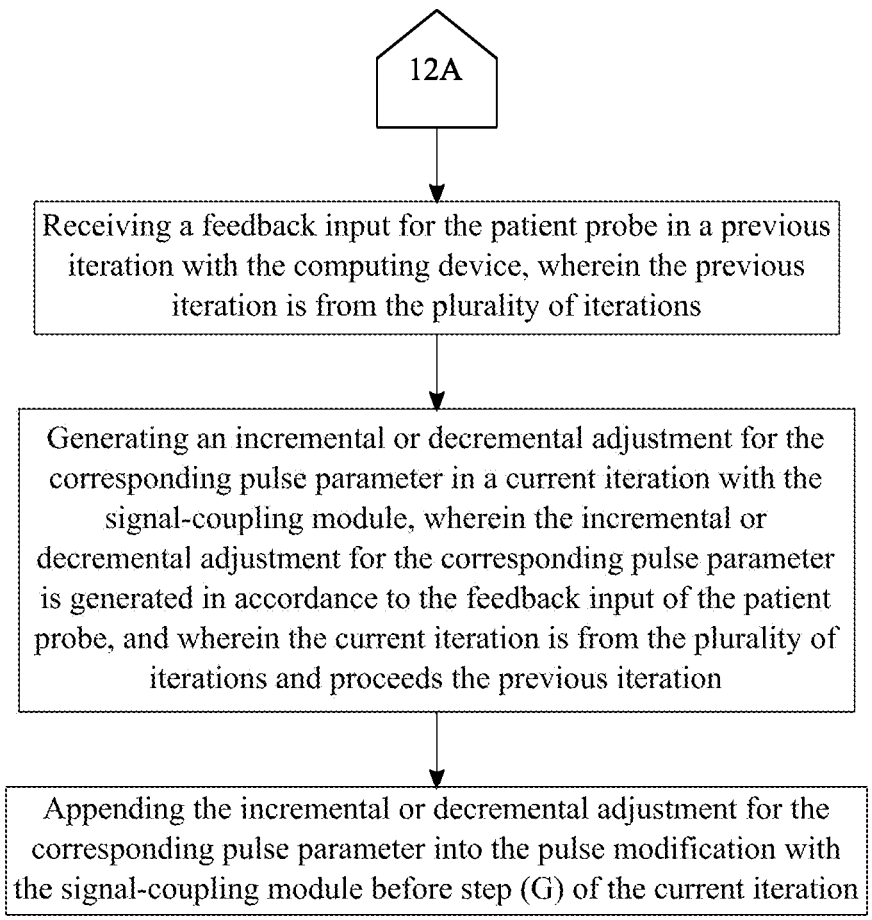
FIG. 12B is a continuation of FIG. 12A.

With reference to FIGS. 12A and 12B, the following subprocess determines the adjustments required for the electrical pulse to comfortably and positively affect the patient. A plurality of iterations is executed for Steps D through I. The computing device is used to receive a feedback input for the patient probe in a previous iteration. As mentioned previously, the feedback input may be any information retrieved following the patient probe such as, but not limited to, a verbal response from the patient or a visual observation of the patient. The previous iteration is from the plurality of iterations. The signal-coupling module is used to generate an incremental or decremental adjustment for the corresponding pulse parameter in a current iteration. The incremental or decremental adjustment for the corresponding pulse parameter is generated in accordance to feedback input of the patient probe. The current iteration is from the plurality of iterations and proceeds the previous iteration. In further detail and in the preferred embodiment, the pulse parameters and adjust steps of choices are the direct current amplitude less than 5.5 mA in step of less than 0.2 mA, pulse width less than 900-μs in step of less than 150-μs, frequency less than 500 Hz in step of less than 100 Hz, pause between pulses less than 20 seconds in varied steps less than 5 seconds, pulse duration less than 5 seconds in step less than 0.5 seconds. Each electrical pulse is delivered less than every 60 seconds in step of less than 15 seconds for not more than 3 hours in step of less than 0.5 hours. The electrical pulse waveforms include, but is not limited to, triangle wave, sawtooth wave, rectangular wave, square wave, and sine wave. The signal-coupling module is used to append the incremental or decremental adjustment for the corresponding pulse parameter into the pulse modification before step G of the current iteration. Thus, the electrical pulse is adjusted to be comfortable and positively-effective for the patient. As disclosed previously, the incremental or decremental adjustment is minimally and maximally limited within the specified parameter range of the corresponding pulse parameter.

Although the invention has been explained in relation to its preferred embodiment, it is to be understood that many other possible modifications and variations can be made without departing from the spirit and scope of the invention as hereinafter claimed.

What is claimed is:
1. A method of coupling acoustic and electrical stimulation of noninvasive neuromodulation for diagnosis and/or treatment, wherein the method comprises the steps of:
(A) providing an acoustic signal generator, an acoustic stimulation module, and an audio output device, wherein the acoustic signal generator, the acoustic stimulation module, and the audio output device is communicably coupled to a computing device, and wherein the acoustic stimulation module is a piece of hardware;
(B) providing an electrical pulse generator, an electrical pulse stimulation module, and an electrode, wherein the electrical pulse generator, the electrical pulse stimulation module, and the electrode is communicably coupled to the computing device, and wherein the electrical pulse stimulation module is a piece of hardware;
(C) providing a signal-coupling module, wherein the signal-coupling module is communicably coupled to the computing device, and wherein the signal-coupling module can be operated manually or automatically, and wherein the signal-coupling module is a piece of hardware;
(D) outputting an initial acoustic signal with the acoustic signal generator;
(E) outputting an initial electrical pulse with the electrical pulse generator;
(F) comparing the initial acoustic signal to the initial electrical pulse with the signal-coupling module in order to identify a signal modification and a pulse modification, wherein the signal modification and the pulse modification respectively couples the initial acoustic signal and the initial electrical pulse to each other;
(G) modulating the initial acoustic signal with the signal modification with the acoustic stimulation module in order to generate a coupled acoustic signal;
(H) modulating the initial electrical pulse with the pulse modification with the electrical pulse stimulation module in order to generate a coupled electrical pulse;
(I) outputting the coupled acoustic signal with the audio output device and/or the coupled electrical pulse with the electrode;
executing a plurality of iterations for steps (D) through (I);
providing a plurality of signal parameters for the initial acoustic signal and providing a plurality of pulse parameters for the initial electrical pulse;
providing a patient probe managed by the computing device, wherein the patient probe is correlated to a probe-associated signal parameter from the plurality of signal parameters, and wherein the patient probe is correlated to a probe-associated pulse parameter from the plurality of pulse parameters, and wherein the patient probe is managed manually or automatically;
receiving a feedback input for the patient probe in a previous iteration with the computing device, wherein the previous iteration is from the plurality of iterations;
generating an incremental or decremental adjustment for the probe-associated signal parameter in a current iteration with the signal-coupling device, if the incremental or decremental adjustment for the probe-associated signal parameter is generated in accordance to the feedback input of the patient probe, wherein the current iteration is from the plurality of iterations and proceeds the previous iteration;

appending the incremental or decremental adjustment for the probe-associated signal parameter into the signal modification with the signal-coupling module before step (G) of the current iteration;

generating an incremental or decremental adjustment for the probe-associated pulse parameter in a current iteration with the signal-coupling device, if the incremental or decremental adjustment for the probe-associated pulse parameter is generated in accordance to the feedback input of the patient probe, wherein the current iteration is from the plurality of iterations and proceeds the previous iteration; and appending the incremental or decremental adjustment for the probe-associated pulse parameter into the pulse modification with the signal-coupling module before step (G) of the current iteration.

2. The method of coupling acoustic and electrical stimulation of noninvasive neuromodulation for diagnosis and/or treatment as claimed in claim 1, wherein the method comprises the steps of:

providing a signal algorithm stored on the signal-coupling module, wherein each signal parameter is correlated to a corresponding pulse parameter from the plurality of pulse parameters by the signal algorithm, and wherein the signal algorithm is experimentally calibrated;

measuring an actual value for each signal parameter with the acoustic signal stimulation module after step (D) but before step (F)

measuring an actual value for the corresponding pulse parameter with the electrical pulse stimulation module after step (E) but before step (F);

executing the signal algorithm with the signal-coupling module in order to convert the actual value for corresponding pulse parameter into a calculated value for each signal parameter during step (F);

calculating a difference for each signal parameter with the signal-coupling module, wherein the difference is between the actual value and the calculated value for each signal parameter during step (F); and compiling the difference for each signal parameter into the signal modification with the signal-coupling module during step (F).

3. The method of coupling acoustic and electrical stimulation of noninvasive neuromodulation for diagnosis and/or treatment as claimed in claim 1, wherein the method comprises the steps of:

providing a signal algorithm stored on the signal-coupling module, wherein each pulse parameter is correlated to a corresponding signal parameter from the plurality of signal parameters by the signal algorithm, and wherein the signal algorithm is experimentally calibrated;

measuring an actual value for each pulse parameter with the electrical pulse stimulation module after step (E) but before step (F);

measuring an actual value for the corresponding signal parameter with the acoustic signal stimulation module after step (D) but before step (F);

executing the signal algorithm with the signal-coupling module in order to convert the actual value for corresponding signal parameter into a calculated value for each pulse parameter during step (F);

calculating a difference for each pulse parameter with the signal-coupling module, wherein the difference is between the actual value and the calculated value for each pulse parameter during step (F); and compiling the difference for each pulse parameter into the pulse modification with the signal-coupling module during step (F).

4. The method of coupling acoustic and electrical stimulation of noninvasive neuromodulation for diagnosis and/or treatment as claimed in claim 1, wherein the audio output device is a pair of headphones.

5. The method of coupling acoustic and electrical stimulation for noninvasive neuromodulation for diagnosis and/or treatment as claimed in claim 1, wherein the audio output device is at least one speaker.

6. The method of coupling acoustic and electrical stimulation of noninvasive neuromodulation for diagnosis and/or treatment as claimed in claim 1, wherein the electrode is a transmucosal electrode.

7. The method of coupling acoustic and electrical stimulation for noninvasive neuromodulation for diagnosis and/or treatment as claimed in claim 1, wherein the electrode is a skin electrode.

8. The method of coupling acoustic and electrical stimulation of noninvasive neuromodulation for diagnosis and/or treatment as claimed in claim 1, wherein the method comprises the step of:

synchronously outputting the coupled acoustic signal with the audio output device and the coupled electrical pulse with the electrode during step (I).

9. The method of coupling acoustic and electrical stimulation of noninvasive neuromodulation for diagnosis and/or treatment as claimed in claim 8, wherein the method comprises the steps of:

prompting a user to synchronously output the coupled acoustic signal and the coupled electrical pulse with the computing device; and executing a synchronous output of the coupled acoustic signal with the audio output device and the coupled electrical pulse with the electrode, if the coupled acoustic signal and the coupled electrical pulse is selected to be synchronously outputted by the computing device.

10. The method of coupling acoustic and electrical stimulation for noninvasive neuromodulation for diagnosis and/or treatment as claimed in claim 1, wherein the method comprises the step of:

asynchronously outputting the coupled acoustic signal with the audio output device during step (I).

11. The method of coupling acoustic and electrical stimulation of noninvasive neuromodulation for diagnosis and/or treatment as claimed in claim 10, wherein the method comprises the steps of:

prompting a user to asynchronously output the coupled acoustic signal or the coupled electrical pulse with the computing device; and executing an asynchronous output of the coupled acoustic signal with the audio output device, if the coupled acoustic signal is selected to be asynchronously outputted by the computing device.

12. The method of coupling acoustic and electrical stimulation for noninvasive neuromodulation for diagnosis and/or treatment as claimed in claim 1, wherein the method comprises the step of:

asynchronously outputting the coupled electrical pulse with the electrode during step (I).

13. The method of coupling acoustic and electrical stimulation of noninvasive neuromodulation for diagnosis and/or treatment as claimed in claim 12, wherein the method comprises the steps of:

prompting a user to asynchronously output the coupled acoustic signal or the coupled electrical pulse with the computing device; and executing an asynchronous output of the coupled electrical pulse with the electrode, if the coupled electrical pulse is selected to be asynchronously outputted by the computing device.

14. The method of coupling acoustic and electrical stimulation for noninvasive neuromodulation for diagnosis and/or treatment as claimed in claim 1 wherein the incremental or decremental adjustment is minimally and maximally limited within a specified parameter range of the corresponding signal parameter.

15. The method of coupling acoustic and electrical stimulation of noninvasive neuromodulation for diagnosis and/or treatment as claimed in claim 1, wherein the incremental or decremental adjustment is minimally and maximally limited within a specified parameter range of the corresponding pulse parameter.

* * * * *